(12) United States Patent
Ferrera

(10) Patent No.: US 6,224,610 B1
(45) Date of Patent: *May 1, 2001

(54) SHAPE MEMORY POLYMER INTRAVASCULAR DELIVERY SYSTEM WITH HEAT TRANSFER MEDIUM

(75) Inventor: David A. Ferrera, San Francisco, CA (US)

(73) Assignee: Micrus Corporation, Mountain View, CA (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/143,904

(22) Filed: Aug. 31, 1998

(51) Int. Cl.[7] .................................................... A61F 11/00
(52) U.S. Cl. ............................................................ 606/108
(58) Field of Search ..................... 606/108, 191, 606/200, 192, 151, 213, 195; 623/12

(56) References Cited

U.S. PATENT DOCUMENTS

| | | |
|---|---|---|
| 3,868,956 | 3/1975 | Alfidi et al. . |
| 4,341,218 | 7/1982 | Ü . |
| 4,346,712 | 8/1982 | Handa et al. . |
| 4,402,319 | 9/1983 | Handa et al. . |
| 4,441,495 | 4/1984 | Hicswa . |
| 4,503,569 * | 3/1985 | Dotter .................. 606/191 |
| 4,545,367 | 10/1985 | Tucci . |
| 4,957,479 | 9/1990 | Roemer . |
| 4,969,890 * | 11/1990 | Sugita et al. .......... 606/192 |
| 4,984,581 * | 1/1991 | Stice ...................... 606/108 |
| 5,026,377 | 6/1991 | Burton et al. . |
| 5,100,429 | 3/1992 | Sinofsky et al. . |
| 5,122,136 | 6/1992 | Guglielmi et al. . |
| 5,151,152 | 9/1992 | Kaeufe et al. . |
| 5,170,801 | 12/1992 | Casper et al. . |
| 5,197,978 | 3/1993 | Hess . |
| 5,250,071 | 10/1993 | Palermo . |
| 5,261,916 | 11/1993 | Engelson . |
| 5,312,152 | 5/1994 | Woebkenberg, Jr. et al. . |
| 5,350,397 | 9/1994 | Palermo et al. . |
| 5,354,295 | 10/1994 | Guglielmi et al. . |
| 5,522,836 | 6/1996 | Palermo . |
| 5,540,713 | 7/1996 | Schnepp-Pesch et al. . |
| 5,545,210 | 8/1996 | Hess et al. . |
| 5,562,698 | 10/1996 | Parker . |
| 5,569,245 | 10/1996 | Guglielmi et al. . |
| 5,601,593 | 2/1997 | Freitag . |
| 5,662,621 * | 9/1997 | Lafontaine ............................ 604/281 |
| 5,716,410 * | 2/1998 | Wang et al. ............................ 623/12 |
| 5,725,546 | 3/1998 | Samson . |

(List continued on next page.)

FOREIGN PATENT DOCUMENTS

| | | |
|---|---|---|
| 41 02 550 A1 | 8/1991 | (DE) . |
| 0 183 372 A1 | 4/1986 | (EP) . |
| 0 382 014 A1 | 8/1990 | (EP) . |
| 0 717 961 A1 | 6/1996 | (EP) . |
| 02255157 | 3/1989 | (JP) . |
| 92/14408 | 9/1992 | (WO) . |
| 94/16629 | 8/1994 | (WO) . |
| 98/22042 | 5/1998 | (WO) . |
| 98/22175 | 5/1998 | (WO) . |

Primary Examiner—Michael Buiz
Assistant Examiner—Tan-Uyen T. Ho
(74) Attorney, Agent, or Firm—Fulwider Patton Lee & Utecht

(57) ABSTRACT

The intravascular delivery system includes an elongated, flexible heat pipe pusher member, a therapeutic device to be placed within the vasculature of a patient, and a shape memory collar detachably mounting the therapeutic device for placement of the therapeutic device within the vasculature. The shape memory collar is disposed either the therapeutic device or the flexible heat pipe pusher member and connects the therapeutic device and the heat pipe pusher member. In a presently preferred embodiment, the shape memory collar is made of nickel titanium alloy.

22 Claims, 1 Drawing Sheet

U.S. PATENT DOCUMENTS

| | | |
|---|---|---|
| 5,746,769 | 5/1998 | Ton et al. . |
| 5,749,894 | 5/1998 | Engelson . |
| 5,800,455 | 9/1998 | Palermo et al. . |
| 5,814,062 | 9/1998 | Sepetka et al. . |
| 5,944,733 * | 8/1999 | Engelson . |
| 5,976,131 | 11/1999 | Guglielmi et al. . |
| 5,984,929 | 11/1999 | Bashiri et al. . |
| 5,988,242 | 11/1999 | Saadat et al. . |

* cited by examiner

SHAPE MEMORY POLYMER INTRAVASCULAR DELIVERY SYSTEM WITH HEAT TRANSFER MEDIUM

BACKGROUND OF THE INVENTION

1. Field of the Invention

This invention relates generally to devices for interventional therapeutic treatment or vascular surgery for treatment of defects in the vasculature, and more particularly concerns a system and method for delivering intravascular interventional devices, such as for treatment of aneurysms.

2. Description of Related Art

Vascular interventional devices such as vasoocclusive devices are typically placed within the vasculature of the human body by use of a catheter. Vascular interventional devices such as stents can be placed within an occluded vessel to facilitate blood flow through the vessel, and vasoocclusive devices are typically either placed within a blood vessel to block the flow of blood through a vessel making up that portion of the vasculature through the formation of an embolus, or are placed within an aneurysm stemming from the vessel to form such an embolus within the aneurysm. Stents can have a wide variety of configurations, but generally need to be placed and then released at a desired location within a blood vessel. Vasoocclusive devices used for these procedures can also have a wide variety of configurations, and aneurysms have been treated with external surgically placed clips, detachable vasoocclusive balloons and embolus generating vasoocclusive devices such as one or more vasoocclusive coils.

The delivery of such vasoocclusive devices have typically been accomplished by a variety of means, including via a catheter in which the device is pushed through an opening at the distal end of the catheter by a pusher to deploy the device. The vasoocclusive devices can be produced in such a way that they will pass through the lumen of a catheter in a linear shape and take on a complex shape as originally formed after being deployed into the area of interest, such as an aneurysm.

Some conventional vasoocclusive devices are operated by pulling or jerking the catheter tip from the balloon, thus potentially compromising the position of the implant. One such device provides for an endovascular wire and tip that can be separated from the holding wire mechanically or electrolytically for the formation of thrombus in blood vessels. However, such devices that release the interventional device by mechanically breaking an intermediate section between the catheter tip and balloon can potentially leave broken or jagged ends that can potentially injure the vasculature.

One conventional releasable balloon catheter used to embolize vascular lesions has a tube portion made of a material such as a hydrophilic polymer, located between the catheter and the balloon, that can be broken by torsion of the tube. The tube can be melted by heating the tube, or can be dissolved in the blood when heated, and electrodes are provided for heating the tube. Another conventional technique for separating a balloon from a balloon catheter involves the melting and breaking of a connecting member made from polyvinyl alcohol or trans-polyisoprene between the balloon and the catheter body, when power is supplied to electrodes provided for heating the connecting member. When the connecting member is heated to temperatures of about 70° C. and slight tension is applied, the balloon can be separated from the main catheter body. However, such devices that release the interventional device by melting or dissolving the intermediate section between the catheter tip and balloon can also potentially release undesirable particles of materials into the bloodstream.

There is therefore a need for a precise method of deploying therapeutic interventional devices without compromising the position of the implant, without presenting broken or jagged ends that can potentially injure the vasculature, and without releasing undesirable particles of materials into the bloodstream.

The transmittal of energy of various types through a catheter to a remote location in the body has been used in the past, both for therapeutic purposes and to perform actuation or chemical reactions for delivery systems. In one such system, a temporary stent formed from a coil of tubular thermoplastic material is delivered activated for use by a heating element. The thermoplastic stent body is introduced into the vessel to be supported and is then heated by the heating element above its softening temperature and expanded to a second dimension in order to support the vessel. Cooling of the stent body allows the stent to temporarily support the vessel, and the stent body can be heated at a later time to soften and remove the stent from the vessel. However, the thermoplastic stent body contains an electrical resistance heating element, and heat is generated in the stent by a current is passed through electrically conductive wires.

An endovascular stent and delivery system is also known in which a partially cured material is delivered to a selected site in a blood vessel and is then crosslinked in the blood vessel by laser light energy delivered to the partially cured material. The delivery system can also use thermal energy as from a resistive heating element, radio frequency energy, or beta rays in order to cause the crosslinking.

A flexible guide is also known that is formed from a two-way shape memory alloy for use in non-invasive procedures. The device comprises an elongated, flexible guide having a core of a shape memory alloy which allows for tip-deflection and rotational movement to the guide wire in response to heating provided by transmission of an electrical current through the shape memory alloy.

Another catheter is known that is composed of a main body fitted with a shape memory alloy, with a liquid injector for supplying a warming liquid such as a physiological saline or transfusion solution when the shape memory alloy is to recover an original shape.

In another delivery system for an occlusive device, energy is transmitted through a catheter to a coil and a polymeric material to occlude an aneurysm. The polymeric material is solidified by light, heat or RF energy emitted from the end of a light or energy emitting device placed outside the distal end of the guiding catheter.

A common problem with such known delivery and activation systems, conveying heat by such methods as warm liquids, light, electrical energy, radio frequency energy or beta rays, is that they are typically highly inefficient or not particularly powerful, so that once a device to be delivered is placed in the desired location, there can be a delay while sufficient thermal energy is conducted to the activation site, or in the process heat energy can be radiated or otherwise lost during transmission. It would therefore be desirable to provide a thermal energy activated delivery system for vascular interventional devices that is highly efficient and immediate, and can allow the delivery of a necessary amount of thermal energy to a specific location for deployment of an interventional device.

Heat pipes are known as extremely efficient heat transfer devices, and are much more efficient than solid metal heat sinks, for example. Such heat pipes typically have a hollow interior chamber that has been evacuated, then filled with a small amount of working fluid, and sealed. When heat is applied to one end, serving as an evaporator end, the fluid vaporizes, and carries the heat in the vaporized working fluid extremely rapidly to the other end, serving as a condenser end, where the latent heat of vaporization is released as the vapor condenses back into liquid form. The working fluid is then carried back in liquid form to the evaporator end by capillary action. There is thus a need for application of a flexible heat pipe for conducting heat to a specific desired site for the purpose of deploying interventional devices such as stents and occlusive devices. The present invention meets these and other needs.

SUMMARY OF THE INVENTION

Briefly, and in general terms, the present invention provides a precise system and method for efficiently and cleanly releasing a therapeutic device such as a vasoocclusive coil, a stent, or other therapeutic device for use in interventional therapy and vascular surgery, and which is particularly adapted to be inserted into a portion of a vasculature for treatment of a body vessel such as an aneurysm without compromising the position of the implant.

In a presently preferred aspect of the invention, the intravascular delivery system for release and deployment of a therapeutic device within the vasculature of a patient comprises an elongated, flexible heat pipe pusher member, a therapeutic device to be placed within the vasculature of a patient, and a shape memory device detachably mounting the therapeutic device for placement of the therapeutic device within the vasculature. The shape memory device has a closed configuration connecting the therapeutic device to the flexible heat pipe pusher member, and an open configuration for detaching and deploying the therapeutic device from the flexible heat pipe pusher member when a desired placement of the therapeutic device within the vasculature is achieved. The shape memory device is typically a shape memory collar disposed on one of the therapeutic device and the flexible heat pipe pusher member and connects the therapeutic device and the heat pipe pusher member, and in a presently preferred embodiment, the shape memory device is a shape memory collar disposed on the distal tip of the flexible heat pipe pusher member and connecting the therapeutic device to the flexible heat pipe pusher member. In a presently preferred embodiment, the shape memory collar is made of nickel titanium alloy.

In a presently preferred aspect of the invention, the elongated, flexible heat pipe pusher member comprises a flexible heat pipe having a hollow interior chamber containing a working fluid, the flexible heat pipe having a metal evaporator end portion for conducting heat to the working fluid in the interior chamber of the heat pipe, a flexible insulated mid-portion, and a metal condenser end portion for conducting heat from the working fluid to the shape memory device. In another presently preferred aspect, the insulated mid-portion comprises an outer covering of resinous material so that the mid-portion does not radiate heat. The flexible heat pipe typically comprises a metal hollow tube, and in a presently preferred embodiment, the metal hollow tube is formed from a beryllium copper alloy. In another presently preferred aspect, the evaporator end portion comprises a stainless steel portion for conducting heat to the metal hollow tube and the working fluid in the interior chamber of the heat pipe, and the condenser end portion is partially covered with polytetrafluoroethylene, leaving a distal end portion of the condenser end portion exposed to transfer heat to the shape memory collar.

The shape memory collar can be heated to thereby assume a configuration disconnecting the therapeutic device and the flexible heat pipe pusher member, and the heat pipe pusher member advantageously can be connected to a heat source for transferring heat to the collar to induce the collar to detach the therapeutic device from the flexible heat pipe pusher member. In one presently preferred embodiment, the therapeutic device comprises a stem, and the collar clamps onto the stem. The therapeutic device can comprise a vasoocclusive coil, a stent, or another similar therapeutic device adapted to be placed in the vasculature.

The invention thus also provides for a method for release and deployment of a therapeutic device within the vasculature of a patient. In a presently preferred embodiment, a therapeutic device to be placed within the vasculature of a patient is provided, an elongated, flexible heat pipe pusher member is provided, and a shape memory device is provided. The shape memory device is detachably mounted to one of the therapeutic device and the elongated, flexible heat pipe pusher member. The therapeutic device is positioned at a desired placement within a patient's vasculature; and the therapeutic device is disconnected from the elongated, flexible heat pipe pusher member, thereby deploying the therapeutic device. In a presently preferred aspect of the method of the invention, the step of disconnecting the therapeutic device from the elongated, flexible heat pipe pusher member comprises causing heat to be transmitted through the flexible heat pipe member to the shape memory collar to heat the shape memory collar to cause the shape memory collar to expand to release the therapeutic device.

These and other aspects and advantages of the invention will become apparent from the following detailed description and the accompanying drawings, which illustrate by way of example the features of the invention.

DETAILED DESCRIPTION OF THE PREFERRED EMBODIMENTS

Figure 1:
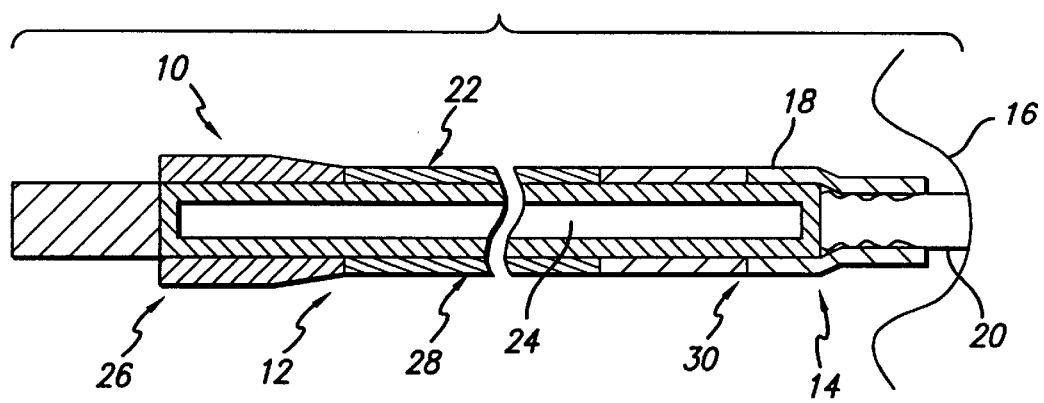
FIG. 1 is an exploded side sectional view of a first preferred embodiment of the heat pipe activated interventional device delivery system of the present invention in which a portion of a therapeutic device is detachably gripped by a shape memory collar mounted to the heat transfer member of the delivery system, showing the shape memory collar in a closed configuration gripping the therapeutic device.

Vasoocclusive devices that are operated by pulling or jerking the catheter tip from the balloon can compromise the position of the implant, while other devices that release such devices by breaking an intermediate section between the catheter tip and balloon can potentially injure the vasculature, and those that melt or dissolve an intermediate section can release undesirable particles of materials into the bloodstream. While the transmittal of energy of various types through a catheter to a remote location in the body has been used in the past, both for therapeutic purposes and to perform actuation or chemical reactions for delivery systems, a common problem with such known delivery and activation systems is that they are typically particularly inefficient.

As is illustrated in the drawings, which are provided for the purposes of illustration and not by way of limitation, the invention is accordingly embodied in an intravascular delivery system for release and deployment of a therapeutic device within the vasculature of a patient. According to the invention, a shape memory collar may be disposed on either the therapeutic device or a flexible heat pipe pusher member, and releasably connects the therapeutic device and the heat pipe pusher member together.

Figure 2:
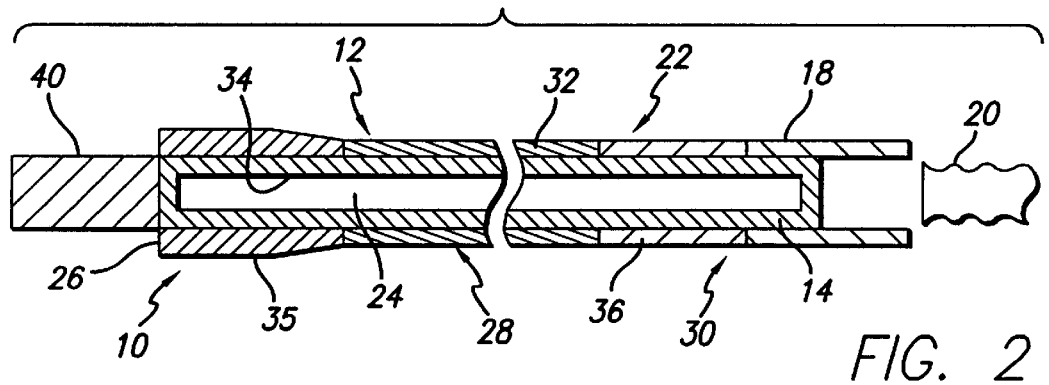
FIG. 2 is an enlarged side sectional view of the heat pipe activated interventional device delivery system of FIG. 1, showing the shape memory collar in an open configuration.

Referring to FIGS. 1 and 2, in a first preferred embodiment, the intravascular delivery system 10 comprises an elongated, flexible heat pipe pusher member 12, having a distal tip 14, and a therapeutic device, such as a coil 16, having at least one configuration which may serve as a vasoocclusive coil or a stent, for example, to be placed within the vasculature of a patient. The therapeutic device is detachably mounted to the distal tip of the pusher member by a shape memory collar 18, for placement of the therapeutic device within the vasculature. The shape memory collar is preferably tubular, having a closed configuration or narrowed configuration with a relatively smaller inner diameter as shown in FIG. 1, connecting the therapeutic device to the flexible heat pipe pusher member, and an open configuration, with a relatively larger inner diameter as shown in FIG. 2, for detaching and deploying the therapeutic device from the flexible heat pipe pusher member when a desired placement of the therapeutic device within the vasculature is achieved. The shape memory collar can, for example, be made of nickel titanium alloy, and the therapeutic device can, for example, be a stent, vasoocclusive coil or wire, having a stem 20 to which a wire coil is mechanically attached, although the wire coil could also be suitably soldered or welded to the stem. The shape memory collar is preferably heat treated in an unextended position, and can be heated to a temperature that allows it to be worked and crimped into an extended position gripping over the end of the stem of the wire coil to connect the therapeutic device to a flexible heat pipe pusher member of the placement catheter shaft.

The elongated, flexible heat pipe pusher member preferably comprises a flexible heat pipe 22 or rod, having a hollow interior chamber 24 that has been evacuated, filled with a small amount of a working fluid, and then sealed. The flexible heat pipe has a metal evaporator end portion 26 for conducting heat to the working fluid in the interior chamber of the heat pipe, a flexible insulated mid-portion 28, and a metal condenser end portion 30 for conducting heat from the working fluid to the shape memory device. The insulated mid-portion preferably has an outer covering 32 of flexible, resinous material so that the mid-portion does not radiate heat. The flexible heat pipe typically is formed from a hollow metal tube 34, and in a presently preferred embodiment, the hollow metal tube is made of an alloy of beryllium and copper. The evaporator end portion preferably comprises a stainless steel portion 35 for conducting heat to the metal hollow tube and the working fluid in the interior chamber of the heat pipe, and the stainless steel evaporator end portion can be formed from a ground stainless steel hypo tube. The condenser end portion is preferably partially covered with polytetrafluoroethylene (PTFE) 36, leaving the distal end portion of the condenser end portion exposed to transfer heat to the shape memory collar.

When the therapeutic device is delivered to an appropriate location in the vasculature, and an operator is satisfied that the device is properly placed, the shape memory collar can be heated, and thereby induced to shrink and pull back to assume a configuration disconnecting the therapeutic device from the placement catheter shaft. The proximal evaporator end of the flexible heat pipe pusher member can thus be connected to a heat source 40, such as an RF heat source or ultrasound heat source, for example, for conducting heat from the proximal evaporator end to the distal condenser end of the flexible heat pipe pusher member and to the shape memory collar at the distal end of the pusher member, to thus heat the collar to return to its previous shape and induce the collar to detach the therapeutic device from the shape memory collar. Heating of the collar can at the same time heat the therapeutic device to cause the therapeutic device to change to a desired configuration.

Figure 3:
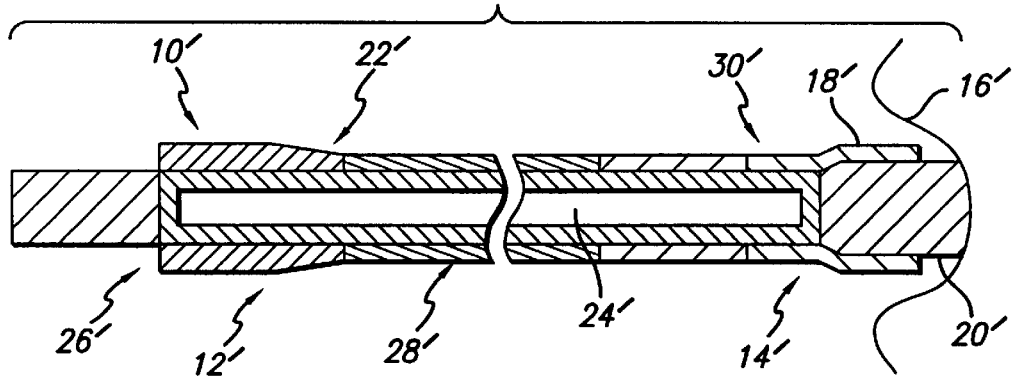
FIG. 3 is an exploded side sectional view of a second preferred embodiment of the heat pipe activated interventional device delivery system of the present invention in which a shape memory collar is mounted to a therapeutic device detachably mounted to the heat transfer member of the delivery system, showing the shape memory collar in a closed configuration gripping the heat transfer member.
Figure 4:
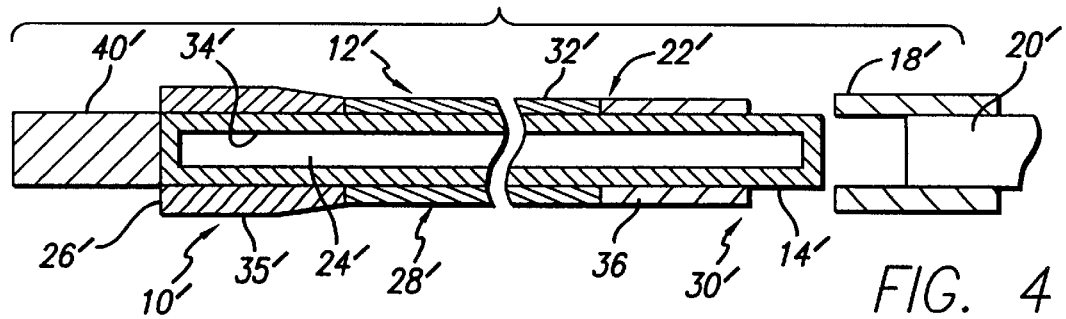
FIG. 4 is an enlarged side sectional view of the heat pipe activated interventional device delivery system of FIG. 3, showing the shape memory collar in an open configuration.

Referring to FIGS. 3 and 4, in a second preferred embodiment, the intravascular delivery system 10' comprises an elongated, flexible heat pipe pusher member 12', having a distal tip 14', and a therapeutic device, such as a coil 16', having at least one configuration which may serve as a vasoocclusive coil or a stent, for example, to be placed within the vasculature of a patient.

In the second preferred embodiment, the shape memory collar 18' can be disposed on the stem 20' of the therapeutic device, and is adapted to be crimped and thus detachably mounted to the distal end 14' of the flexible heat pipe pusher member, for placement of the therapeutic device within the vasculature. The shape memory collar is preferably tubular, having a closed configuration or narrowed configuration with a relatively smaller inner diameter as shown in FIG. 3, connecting the therapeutic device to the flexible heat pipe pusher member, and an open configuration, with a relatively larger inner diameter as shown in FIG. 4, for detaching and deploying the therapeutic device from the flexible heat pipe pusher member when a desired placement of the therapeutic device within the vasculature is achieved. The shape memory collar is preferably heat treated in an unextended position, and can be heated to a temperature that allows it to be worked and crimped into an extended position gripping over the end of the stem of the wire coil to connect the therapeutic device to a flexible heat pipe pusher member of the placement catheter shaft.

The elongated, flexible heat pipe pusher member preferably comprises a flexible heat pipe 22' or rod, having a hollow interior chamber 24' that has been evacuated, filled with a small amount of a working fluid, and then sealed. The flexible heat pipe has a metal evaporator end portion 26' for conducting heat to the working fluid in the interior chamber of the heat pipe, a flexible insulated mid-portion 28', and a metal condenser end portion 30' for conducting heat from the working fluid to the shape memory device. The insulated mid-portion preferably has an outer covering 32' of flexible, resinous material so that the mid-portion does not radiate heat. The flexible heat pipe typically is formed from a hollow metal tube 34', and in a presently preferred embodiment, the hollow metal tube is made of an alloy of beryllium and copper. The evaporator end portion preferably comprises a stainless steel portion 35' for conducting heat to the metal hollow tube and the working fluid in the interior chamber of the heat pipe, and the stainless steel evaporator end portion can be formed from a ground stainless steel hypo tube. The condenser end portion is preferably partially covered with a coating 36' of PTFE, leaving the distal end portion of the condenser end portion exposed to transfer heat to the shape memory collar.

The proximal evaporator end of the flexible heat pipe pusher member can be connected to a heat source 40', such as an RF heat source or ultrasound heat source, for example, for conducting heat from the proximal evaporator end to the distal condenser end of the flexible heat pipe pusher member and to the shape memory collar at the distal end of the pusher member, to thus heat the collar to return to its previous shape and induce the collar to detach the therapeutic device from the shape memory collar.

In a presently preferred embodiment, the shape memory collar is formed from a shape memory material such as nickel titanium alloy, that can be heat treated to have shape memory behavior, such that the alloy has a desired closed configuration at a temperature appropriate for introduction into the body, and after placement, the collar will take on a more open shape for detaching the therapeutic device from the flexible, heat pipe pusher member. Those skilled in the art will recognize that the invention can also be used with a variety of other placement catheter systems, and it is not intended that the invention be limited to the placement concepts illustrated by way of example.

It will be apparent from the foregoing that while particular forms of the invention have been illustrated and described, various modifications can be made without departing from the spirit and scope of the invention. Accordingly, it is not intended that the invention be limited, except as by the appended claims.

What is claimed is:

1. An intravascular delivery system for release and deployment of a therapeutic device within the vasculature of a patient, comprising:

an elongated, flexible heat pipe pusher member, said elongated, flexible heat pipe pusher member comprising a flexible heat pipe having a hollow interior chamber containing a working fluid, said flexible heat pipe having a metal evaporator end portion for conducting heat to the working fluid in the interior chamber of the heat pipe, a flexible insulated mid-portion, and a metal condenser end portion for conducting heat from the working fluid;

a therapeutic device to be placed within the vasculature of a patient; and a shape memory connector receiving heat from the shape memory connector and detachably mounting the therapeutic device to the flexible heat pipe pusher member for placement of the therapeutic device within the vasculature, said shape memory connector having a closed configuration connecting the therapeutic device to the flexible heat pipe pusher member, and an open configuration for detaching and deploying the therapeutic device from the flexible heat pipe pusher member when a desired placement of the therapeutic device within the vasculature is achieved.

2. The intravascular delivery system of claim 1, wherein said shape memory connector is a shape memory collar disposed on one of the therapeutic device and the flexible heat pipe pusher member and connecting the therapeutic device and the heat pipe pusher member.

3. The intravascular delivery system of claim 1, wherein said shape memory connector is a shape memory collar disposed on the distal tip of the flexible heat pipe pusher member and connecting the therapeutic device to the flexible heat pipe pusher member.

4. The intravascular delivery system of claim 1, wherein said insulated mid-portion comprises an outer covering of resinous material so that the mid-portion does not radiate heat.

5. The intravascular delivery system of claim 1, wherein said flexible heat pipe comprises a metal hollow tube.

6. The intravascular delivery system of claim 5, wherein said metal hollow tube is formed from a beryllium copper alloy.

7. The intravascular delivery system of claim 1, wherein said evaporator end portion comprises a stainless steel portion for conducting heat to said metal hollow tube and the working fluid in the interior chamber of the heat pipe.

8. The intravascular delivery system of claim 1, wherein said condenser end portion is partially covered with polytetrafluoroethylene, leaving a distal end portion of the condenser end portion exposed to transfer heat to the shape memory connector.

9. The intravascular delivery system of claim 2, wherein said shape memory collar can be heated to thereby assume a configuration disconnecting the therapeutic device and the flexible heat pipe pusher member.

10. The intravascular delivery system of claim 2, wherein said heat pipe pusher member is connected to a heat source for transferring heat to the collar to induce the collar to detach the therapeutic device from the flexible heat pipe pusher member.

11. The intravascular delivery system of claim 3, wherein said therapeutic device comprises a stem, and said collar clamps onto said stem.

12. The intravascular delivery system of claim 2, wherein said shape memory collar is made of nickel titanium alloy.

13. The intravascular delivery system of claim 1, wherein said therapeutic device comprises a vasoocclusive coil.

14. The intravascular delivery system of claim 1, wherein said therapeutic device comprises a stent.

15. A method for release and deployment of a therapeutic device within the vasculature of a patient, the steps of the method comprising:

providing a therapeutic device to be placed within the vasculature of a patient;

providing an elongated, flexible heat pipe pusher member;

providing a shape memory connector;

detachably mounting said shape memory connector to one of said therapeutic device and said elongated, flexible heat pipe pusher member for detachably mounting said therapeutic device to the flexible heat pipe pusher member, said shape memory connector having a closed configuration connecting the therapeutic device to the flexible heat pipe pusher member, and an open configuration for detaching and deploying the therapeutic device from the flexible heat pipe pusher member when a desired placement of the therapeutic device within a patient's vasculature is achieved;

positioning the therapeutic device at a desired placement within a patient's vasculature; and disconnecting the therapeutic device from the elongated, flexible heat pipe pusher member, thereby deploying the therapeutic device.

16. The method of claim 15, wherein said step of disconnecting the therapeutic device from the elongated, flexible heat pipe pusher member comprises causing heat to be transmitted through the flexible heat pipe member to the shape memory connector to heat the shape memory connector to cause the shape memory collar to expand to release the therapeutic device.

17. An intravascular delivery system for release and deployment of a therapeutic device within the vasculature of a patient, comprising:

an elongated, flexible heat pipe pusher member comprising a flexible heat pipe having a hollow interior chamber containing a working fluid, said flexible heat pipe having a metal evaporator end portion for conducting heat to the working fluid in the interior chamber of the heat pipe, a flexible insulated mid-portion, and a metal condenser end portion for conducting heat from the working fluid to the shape memory device;

a therapeutic device to be placed within the vasculature of a patient; and a shape memory device detachably mounting the therapeutic device for placement of the therapeutic device within the vasculature, said metal condenser end portion of the flexible heat pipe pusher member conducting heat from the working fluid to the shape memory device, said shape memory device having a closed configuration connecting the therapeutic device to the flexible heat pipe pusher member, and an open configuration for detaching and deploying the therapeutic device from the flexible heat pipe pusher member responsive to heat conducted from the flexible heat pipe pusher member to the shape memory device when a desired placement of the therapeutic device within the vasculature is achieved.

18. The intravascular delivery system of claim 17, wherein said insulated mid-portion comprises an outer covering of resinous material so that the mid-portion does not radiate heat.

19. The intravascular delivery system of claim 17, wherein said flexible heat pipe comprises a metal hollow tube.

20. The intravascular delivery system of claim 19, wherein said metal hollow tube is formed from a beryllium copper alloy.

21. The intravascular delivery system of claim 17, wherein said evaporator end portion comprises a stainless steel portion for conducting heat to said metal hollow tube and the working fluid in the interior chamber of the heat pipe.

22. The intravascular delivery system of claim 17, wherein said condenser end portion is partially covered with polytetrafluoroethylene, leaving a distal end portion of the condenser end portion exposed to transfer heat to the shape memory device.

* * * * *